US00PP34064P2

(12) United States Plant Patent
Masor

(10) Patent No.: US PP34,064 P2
(45) Date of Patent: Mar. 22, 2022

(54) ***CALIBRACHOA* PLANT NAMED 'BALCHARED'**

(50) Latin Name: ***Calibrachoa* x *hybrida***
Varietal Denomination: Balchared

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/501,697

(22) Filed: Oct. 14, 2021

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — Audrey Charles

(57) ABSTRACT

A new and distinct cultivar of *Calibrachoa* plant named 'Balchared', characterized by its dark red-colored flowers, medium green-colored foliage, and vigorous, mounded-trailing growth habit, is disclosed.

1 Drawing Sheet

Latin name of genus and species of plant claimed: *Calibrachoa* x *hybrida*.
Variety denomination: 'Balchared'.

BACKGROUND OF THE INVENTION

The present invention relates to a new and distinct cultivar of *Calibrachoa* plant botanically known as *Calibrachoa* x *hybrida* and hereinafter referred to by the cultivar name 'Balchared'.

The new cultivar originated in a controlled breeding program in Guadalupe, Calif. during October 2019. The objective of the breeding program was the development of *Calibrachoa* cultivars with attractive novelty flower coloration, and a vigorous, mounded-trailing growth habit.

The new *Calibrachoa* cultivar is the result of cross-pollination. The female (seed) parent of the new cultivar is the proprietary *Calibrachoa* x *hybrida* breeding selection coded CAL-15282-01, not patented, characterized by its medium red-colored flowers, medium green-colored foliage, and moderately vigorous, mounded-trailing growth habit. The male (pollen) parent of the new cultivar is the proprietary *Calibrachoa* x *hybrida* breeding selection coded CAL-15818-04, not patented, characterized by its medium red-colored flowers, medium green-colored foliage, low growth vigor, and compact-mounded growth habit. The new cultivar was selected as a single flowering plant within the progeny of the above stated cross-pollination during March 2020 in a controlled environment in Arroyo Grande, Calif.

Asexual reproduction of the new cultivar by terminal stem cuttings since March 2020 in Arroyo Grande, Calif. and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balchared' as a new and distinct cultivar of *Calibrachoa* plant:

1. Dark red-colored flowers;
2. Medium green-colored foliage; and
3. Vigorous, mounded-trailing growth habit.

Plants of the new cultivar differ from plants of the female and male parents primarily in having darker red-colored flowers and increased growth vigor.

Of the many commercially available *Calibrachoa* cultivars, the most similar in comparison to the new cultivar is CABARET Red 'Balcabred20', U.S. Plant Pat. No. 31,956. However, in side-by-side comparisons, plants of the new cultivar differ from plants of 'Balcabred20' in at least the following characteristics:

1. Plants of the new cultivar have darker red-colored flowers than plants of 'Balcabred20';
2. Plants of the new cultivar have larger diameter corollas than plants of 'Balcabred20'; and
3. Plants of the new cultivar have larger leaves than plants of 'Balcabred20'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balchared'. The plants were approximately 5-months old. The plants were grown in 3-gallon containers for approximately 10 weeks in an outdoor nursery in West Chicago, Ill. Plants were pinched twice prior to transplant.

DETAILED BOTANICAL DESCRIPTION

Figure 1:
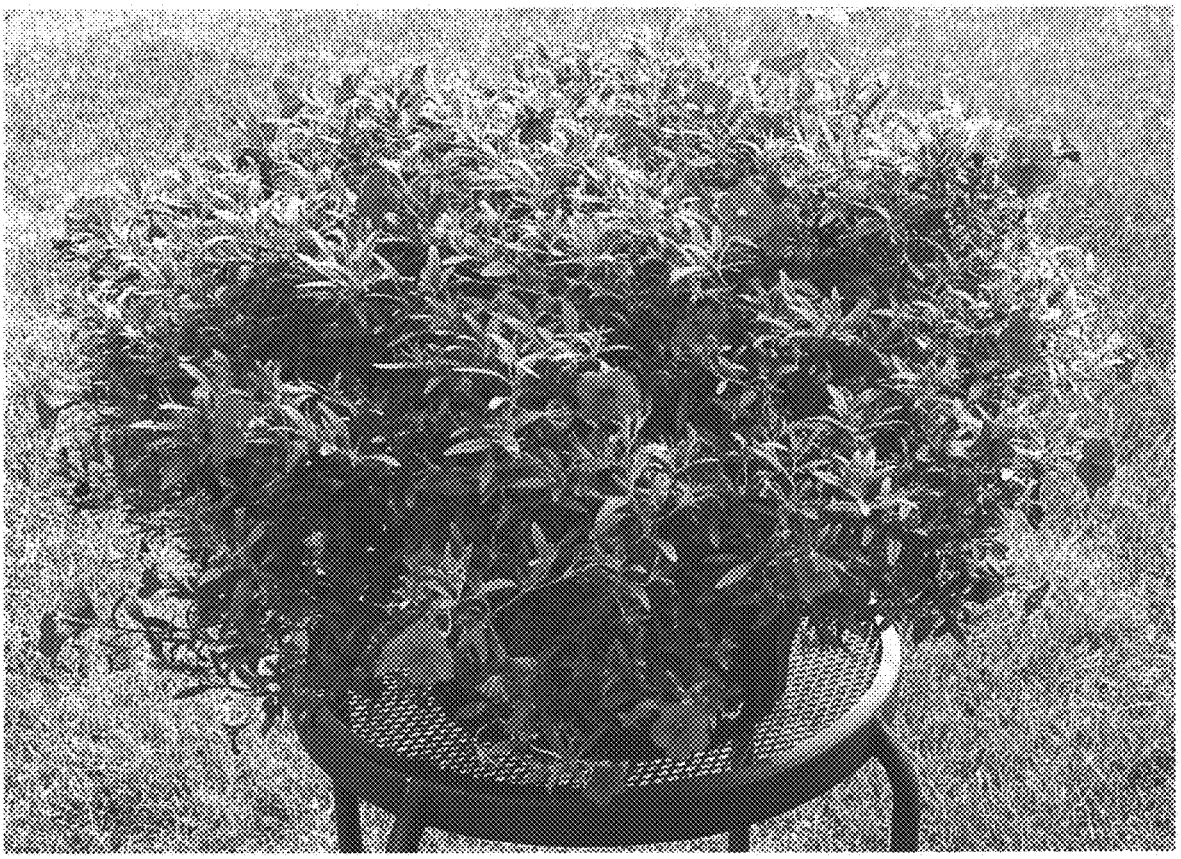
FIG. 1 illustrates a side view of the overall growth and flowering habit of 'Balchared'.
Figure 2:
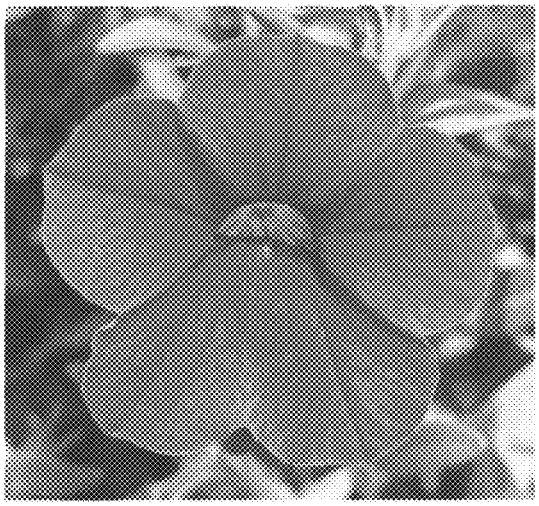
FIG. 2 illustrates a close-up view of an individual flower of 'Balchared'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately 5-month-old plants produced from cuttings from stock plants and grown under conditions comparable to those used in commercial practice. The plants were grown in 3-gallon containers for approximately 10 weeks in an outdoor nursery in West Chicago, Ill. Plants were given two pinches prior to transplant. Prior to transplant plants were grown in a polycarbonate greenhouse in West Chicago, Ill. Greenhouse temperatures were maintained at approximately 70° F. to 85° F. (21° C. to 29° C.) during the day and approximately 60° F. to 70° F. (16° C. to 21° C.) during the night. Supplemental lighting was used during propagation stage. Measurements and numerical values represent averages of typical plants.

Botanical classification: *Calibrachoa* x *hybrida* 'Balchared'.

Parentage:

*Female parent.*—Proprietary *Calibrachoa* x *hybrida* breeding selection coded CAL-15282-01, not patented.

*Male parent.*—Proprietary *Calibrachoa* x *hybrida* breeding selection coded CAL-15818-04, not patented.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 9 weeks from a rooted cutting to finish in a 10 cm pot.

*Growth habit and general appearance.*—Vigorous, mounded-trailing.

*Size.*—Height from soil level to top of plant plane: Approximately 22.0 cm. Width: Approximately 67.0 cm.

*Branching habit.*—Freely branching, pinching enhances basal branching. Quantity of main branches per plant: Approximately 10.

*Branch.*—Strength: Moderate. Length: Approximately 31.0 cm. Diameter: Approximately 2.0 mm to 3.0 mm. Length of central internode: Approximately 2.3 cm. Texture: Densely pubescent with a mixture of non-glandular and glandular hairs. Gland color: Colorless, transparent. Color of young stems: Color of young stems: 146C occasionally tinted with N186A. Color of mature stems: 146D with age becoming woody 199C.

Foliage description:

*General description.*—Fragrance: None detected. Form: Simple. Arrangement on flowering stem: Opposite.

*Leaves.*—Aspect: At acute angle to stem with tip turning downward. Shape: Elliptic. Margin: Entire. Apex: Broadly acute. Base: Attenuate. Venation pattern: Pinnate. Length of mature leaf: Approximately 3.5 cm. Width of mature leaf: Approximately 9.0 mm. Texture of upper and lower surfaces: Moderately glandular pubescent. Gland color: Colorless, transparent. Color of upper surface of young and mature foliage: 137B with midvein of 146C. Color of lower surface of young and mature foliage: Closest to 138B with midvein of 146D.

*Petiole.*—Length: Approximately 4.0 mm. Diameter: Approximately 2.0 mm. Texture: Moderately glandular pubescent. Gland color: Colorless, transparent. Color: 146D.

Flowering description:

*Flowering habit.*—'Balchared' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single, salverform. Quantity per plant: Approximately 55. Fragrance: None detected.

*Bud.*—Rate of opening: Generally takes 3 to 4 days for bud to progress from first color to fully open flower. Quantity per plant: Approximately 23.

*Bud just before opening.*—Shape: Oblong. Length: Approximately 2.1 cm. Diameter: Approximately 5.0 mm. Texture: Densely glandular pubescent. Gland color: Colorless, transparent. Color: Petal portion closest to 185C, tube portion 154C, venation of 144A with N77A.

*Corolla.*—Diameter: Approximately 3.2 cm.

*Petals.*—Quantity: 5, fused to form a tube. Shape: Obovate. Margin: Entire. Apex: Obtuse to broadly minutely acute. Length from tube: Approximately 1.4 cm. Length of free portion: Approximately 6.0 mm. Width: Approximately 1.5 cm. Texture of upper surface: Glabrous. Texture of lower surface: Glandular pubescent, dense along venation. Gland color: Colorless, transparent. Color of upper surface when first open: 53A and N45A with an overlay of N77A at throat opening; midveins of N77A. Color of lower surface when first and fully open: 185C to 185D midveins of 144A with N77A. Color of upper surface when fully open: 53A and N45A to N45B with an overlay of N77A at throat opening; midveins of N77A.

*Corolla tube.*—Length: Approximately 1.7 cm. Diameter at distal end: Approximately 5.0 mm. Diameter at proximal end: Approximately 1.0 mm. Texture of inner surface: Glabrous. Texture of outer surface: Densely glandular pubescent. Gland color: Colorless, transparent. Color of inner surface: 13B with venation of N77A. Color of outer surface: 154C with venation of 144A and N77A.

*Sepals.*—Quantity per flower: 5, fused at base. Shape: Lanceolate. Apex: Acute. Length: Approximately 1.3 cm. Width: Approximately 2.5 mm. Texture of upper and lower surfaces: Densely glandular pubescent. Gland color: Colorless, transparent. Color of upper surface: Color of upper surface: 137A. Color of lower surface: 137B with base of 146D.

*Peduncle.*—Strength: Strong, flexible. Aspect: Acute angle to stem. Length: Approximately 1.2 cm to 1.8 cm. Diameter: Approximately 1.0 mm. Texture: Densely glandular pubescent. Gland color: Colorless, transparent. Color: 146D.

*Reproductive organs.*—Androecium: Stamen quantity: 5, basifixed. Stamen length: Approximately 1.2 cm. Filament length of fixed portion: Approximately 4.0 mm. Filament color: 150D. Anther shape: Bilobed, ovoid. Anther length: Approximately 1.0 mm. Anther color: 8C. Pollen amount: Abundant. Pollen color: 8D. Gynoecium: Pistil quantity: 1 per flower. Pistil length: Approximately 1.1 cm. Stigma shape: Funnel. Stigma length: Less than 1.0 mm. Stigma color: 146D. Style length: Approximately 9.0 mm. Style color: 145D. Ovary diameter: Approximately 2.0 mm. Ovary color: 145B.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balchared', substantially as herein illustrated and described.

* * * * *